United States Patent [19]
Biola et al.

[11] 3,935,276
[45] Jan. 27, 1976

[54] PROCESS FOR THE MANUFACTURE OF METHYL MERCAPTAN

[75] Inventors: Georges Biola, Venissieux; Bernard Buathier; André Combes, both of Lyon; Michel Martin, Les Roches-de-Condrieu, all of France

[73] Assignee: Rhone-Poulenc Industries, Decines, France

[22] Filed: Aug. 28, 1974

[21] Appl. No.: 501,293

[30] Foreign Application Priority Data
Nov. 30, 1973 France .................... 73.43539

[52] U.S. Cl. ............................................ 260/609 R
[51] Int. Cl.² .......................................... C07C 148/00
[58] Field of Search ...................... 260/609 R, 974

[56] References Cited
UNITED STATES PATENTS

| | | | |
|---|---|---|---|
| 2,822,400 | 2/1958 | Cinque et al. | 260/609 R |
| 2,822,401 | 2/1958 | Hoot et al. | 260/609 R |
| 3,723,580 | 3/1973 | Ito et al. | 260/974 |

*Primary Examiner*—Lewis Gotts
*Assistant Examiner*—D. R. Phillips
*Attorney, Agent, or Firm*—Bacon & Thomas

[57] ABSTRACT

Process for the synthesis of methyl mercaptan by the reaction of methanol with hydrogen sulfide wherein a high degree of conversion and enhanced selectivity for the product are obtained by dividing the quantity of catalyst utilized in the reaction into a minimum of three separate portions to form a plurality of reactive catalyst zones and introducing the total amount of hydrogen sulfide reagent into the first of such catalyst zones and thereafter introducing equivalent or alternatively different amounts of the methanol reagent into the consecutive interconnected catalytic zones to react with hydrogen sulfide flowing therethrough while maintaining a molar ratio of hydrogen sulfide to methanol between 1.1 and 2.5. By subdividing the catalyst into separate beds and introducing the reagents consecutively into the catalytic zones, it is possible to maintain the temperature of the reaction mixture within the optimum range and, therefore, to minimize deterioration of the catalyst due to excessive temperature and substantially eliminate the formation of undesired by-products.

14 Claims, No Drawings

PROCESS FOR THE MANUFACTURE OF METHYL MERCAPTAN

BACKGROUND OF THE INVENTION

The present invention relates to a process for the synthesis of methyl mercaptan from hydrogen sulfide and methanol.

Although methyl mercaptan can be produced catalytically from various starting materials, such as carbon disulfide, carbon monoxide or methane, the most important method from a commercial standpoint consists of reacting hydrogen sulfide and methanol in the vapor phase in the presence of a catalyst essentially as described by Sabatier in 1910 (P. Sabatier, and A. Mailhe, compterendu 150, 832-6, 1569-72, 1217-21, 1910). Since that time, it has been possible to gradually increase the degree of methanol conversion above the 50% level obtained by Sabatier et al by utilizing more effective catalysts. Today, due especially to the use of catalysts based on activated alumina and promoters such as potassium oxides or salts, the problem posed by the synthesis of methyl mercaptan is no longer so much that of the degree of conversion of methanol as that of the selectivity of the reaction for the desired product. In the course of the reaction, a number of objectionable by-products are formed, the primary one being dimethyl sulfide.

It has previously been recognized that the degree of methanol conversion is increased by increasing the temperature of the reaction, while the selectivity in favor of methyl mercaptan is decreased by elevated temperature conditions. Moreover, a temperature threshold exists below which the reaction is not initiated when employing the usual catalysts based on alumina. In practice, therefore, the reactants are introduced into the catalyst mixture at a temperature above 280°C. Since the reaction is exothermic, the reaction temperature rapidly escalates, and this, as stated above, favorably affects the degree of conversion of the methanol but adversely affects the selectivity of the reaction. As disclosed in French Pat. No. 1,161,066, filed June 22, 1956, maintaining the reaction mixture at a uniform temperature very selectively promotes the formation of methyl mercaptan and, consequently, minimizes undesired by-products such as dimethyl sulfide. It can readily be seen then that controlling the temperature is a significant consideration in carrying out the synthesis of methyl mercaptan.

The temperature control method proposed in the abovementioned French patent involves a combination of external and internal temperature regulative means. Externally, the reaction mixture is cooled by any means which makes it possible to remove heat from the reaction mixture, for example, by using a tubular reactor through which a heat exchange fluid, such as air or an organic liquid with a high boiling point, flows. Internal temperature regulation is achieved by utilizing a high molar ratio of hydrogen sulfide to methanol (greater than 2.5) making it possible to use the excess hydrogen sulfide as a heat absorbing agent, and moreover, promoting the formation of methyl mercaptan due to the increased selectivity of the reaction observed with a high $H_2S/CH_3OH$ molar ratio.

While the foregoing solution has proved to be valuable, there are a number of disadvantages associated therewith. One such disadvantage is the necessity of using means external to the reaction to control the temperature instead of confining control to the regulation of reaction parameters. The distinctive drawback of utilizing external control is that it makes it extremely difficult to rapidly lower the reaction temperature in the event of serious exothermic conditions. Moreover, as a consequence of the elevated temperature prevailing in the reaction system and the fluctuation thereof occasioned by unstable exothermic conditions, the selection of the proper heat exchange fluid is necessarily somewhat arbitrary which gives rise to unpredictable temperature control often resulting in serious deterioration and corrosion within the reactor. It should also be noted that even where optimum heat exchange conditions exist, a severe hot spot is observed at the inlet to the reactor causing premature destruction of the catalyst as well as the increased production of methanol cracking products. While the deleterious affect on the catalyst can be partially avoided by diluting the catalyst in the inlet zone, this presents difficult charging problems and problems related to maintaining the homogeneity of the catalyst charge in the reactor.

The utilization of a high $H_2S/CH_3OH$ molar ratio represents a serious disadvantage in the sense that it necessitates making the reactor unit larger to accommodate the excess feed, resulting in higher investment and operating costs. Moreover, a large excess of hydrogen sulfide leads to a reduction in the amount of methyl mercaptan recovered as a result of the entrainment of the product in the uncondensed gases removed after the reaction.

SUMMARY OF THE INVENTION

It is, therefore, a primary object of the instant invention to provide a process for the synthesis of methyl mercaptan from hydrogen sulfide and methanol, wherein the problems and disadvantages associated with prior art methods are obviated.

A further object of the invention is to provide a process for the preparation of methyl mercaptan wherein a high degree of conversion of the methanol reactant is achieved resulting in enhanced yield of the product while at the same time avoiding the formation of undesired by-products.

Another object of the present invention is to provide a method for controlling the temperature of the reaction system within a prescribed optimum range and wherein temperature regulation is obtained by selectively adjusting the quantity of catalyst in contact with the reactants at any point in a reactor as well as by controlling the relative molar ratio of the hydrogen sulfide and methanol reactants in the system.

These and other objects and advantages are accomplished in accordance with the process of the present invention which comprises reacting hydrogen sulfide and methanol to form methyl mercaptan under vapor phase conditions at elevated temperature and pressure and in the presence of suitable catalysts and, optionally, promoters and wherein optimum temperature control within the reaction system is attained by dividing the catalyst into at least three separate portions to establish a series of reactive catalytic zones and introducing the total amount of hydrogen sulfide reagent into the first of such catalytic zones and thereafter injecting predetermined portions of methanol reagent into the consecutive interconnected catalytic zones to effectuate the reaction with hydrogen sulfide flowing therethrough.

DETAILED DESCRIPTION OF THE INVENTION

In accordance with the process of the instant invention, essential temperature control in the synthesis of methyl mercaptan is achieved entirely within the reaction system by modifying certain process parameters without the necessity of utilizing any form of external cooling means such as water jackets or heat exchangers.

Applicants have found that such internal temperature control can be accomplished simply and effectively by dividing the amount of catalyst to be charged to the reactor into at least three separate portions containing the same or different quantities of catalytic component to form a plurality of reactive catalytic zones through which the hydrogen sulfide and methanol reagents in particular predetermined amounts are passed. In practice, the division of the catalyst is achieved by using either a single reactor equipped with plates which are spaced apart and contain a portion of the catalyst, or a series of reactors containing the necessary amounts of catalyst. In tests carried out by the applicants it has been found that for a $H_2S/CH_3OH$ molar ratio of less than 2.5, and at the temperature required for initiating the reaction which is on the order of about 280°C., it is not possible to use any fewer than three catalyst beds without causing the temperature to exceed that at which the catalyst deteriorates and undesirable methanol cracking derivatives are formed. On the other hand, there does not appear to be any definite upper limit for the number of catalyst beds or zones which can be utilized although technological and economic constraints may, in fact, necessitate employing not more than approximately 15.

The catalyst charged to the reactor is advantageously in the form of solid particles such as balls or pellets having a diameter of 1 to 10 mm.

As stated hereinabove, the relative amounts of reagents and the order in which they are introduced into the reactor also affect the temperature levels reached therein and, therefore, according to the present process all of the hydrogen sulfide is introduced at the level of the first catalyst bed, while the methanol reagent is injected in predetermined portions at the inlet to each of the successive catalyst zones. The amounts of methanol reagent introduced may be distributed equally or unequally over all of the beds. Moreover, it is possible to distribute the entire methanol charge over all of the catalyst beds except for a few units, in order to use the latter units as zones for completing the reaction. For example, if the catalyst is divided into ten consecutive beds, the methanol charge may then be divided into nine equal portions, each being introduced at the level of the first nine beds and the last bed utilized for completing the reaction.

In one preferred embodiment of the invention, the catalytic process is continuous inasmuch as the catalyst is first charged to the reactor and thereafter the reagents are continuously fed to the catalytic zones at a predetermined rate.

According to a preferred embodiment of the invention, the apparatus utilized to introduced the methanol into the reactor is selected so as to permit the injection of the latter partially in liquid form and partially in gas form. The methanol heat of evaporation thus absorbs all or part of the heat generated by the reaction. By regulating the proportion of methanol introduced in liquid form depending on the desired temperature for the reagents at the inlet of a particular catalyst bed, it is, therefore, possible to effectively control the temperature of the reaction.

Another aspect of the invention consists of utilizing an overall $H_2S/CH_3OH$ molar ratio of between 1.10 and 2.5. By means of the multiple injection technique described above, it is possible to enhance the selectivity of the reaction in favor of methyl mercaptan despite the fact that the molar ratio is considerably lower than conventionally employed. Inasmuch as the present process does not require a substantial excess of hydrogen sulfide, it is particularly advantageous from an economic standpoint since the size of the reactors, pipelines, pumps and the like can be significantly reduced in comparison to prior art apparatus used in connection with the preparation of methyl mercaptan.

Another aspect of the invention comprises selecting as the catatlyst an activated alumina, the specific surface area of which is between 100 and 350 $m^2/g$ in contrast to prior art catalysts which frequently are aluminas having a low surface area.

Moreover, in order further to improve the selectivity of the reaction, it is possible to use a promoter which may be selected from any of the promoters heretofore known in the art and suitable for carrying out the invention process. However, particularly effective promoters are metal sulfides, such as cadmium sulfide, or potassium salts and oxides such as potassium carbonate and potassium tungstate.

The amounts of catalyst and promoters utilized in practicing the invention are not critical and, therefore, conventionally employed quantities of same, such as suggested in the aforementioned French patent, may be utilized without adversely affecting temperature control within the system.

The temperature at all points throughout the reaction system should be between about 280°C. and 450°C., and preferably between about 320°C. and 370°C. for the reasons given above. The pressure in the reactor or reactors will normally be maintained between 2.5 and 25 bars, and preferably between about 7 and 12 bars. Below 2.5 bars, with a $H_2S/CH_3OH$ molar ratio of less than 2.5, the degree of conversion of the methanol declines considerably whereas recourse to higher pressures on the order of 20 bars makes it possible to increase the recovery of the mercaptan product. Since hydrogen sulfide can be completely condensed, the quantity of mercaptan entrained in the gas phase is reduced to trace amounts. However, the choice of the pressure to be employed in the process is ultimately determined by weighing the advantages of increased conversion against the increased investment and operating costs involved in high pressure equipment.

The methyl mercaptan product is isolated from the reaction effluent in accordance with conventional distillation and decanting techniques.

The invention is further described by the following examples which are merely illustrative of specific modes of practicing the invention and are not intended to limit the scope of the present invention as defined by the appended claims.

EXAMPLE 1

A reaction system for the synthesis of methyl mercaptan was installed and comprised 10 reactors each containing nine liters of catalyst and 2 completion zones of the same volume. The catalyst consisted of activated alumina having a specific surface area of 350 m²/g and into which was incorporated approximately 10% by weight of potassium tungstate. 470 moles per hour of methanol were introduced into the system distributed equally over the first ten reactors. Each portion of methanol introduced was approximately 60% to 40% in liquid form with the remainder in gaseous form, the proportion decreasing uniformly from the second to the last reactor.

Additional operating conditions were as follows:
overall $H_2S/CH_3OH$ molar ratio = 1.8,
temperature at which the reagents were introduced into the first reactor = 320°C.
pressure = 8 bars.

The following results were obtained:
maximum temperature in the system: 374°C.,
degree of conversion of methanol: 98.5%,
selectivity of the conversion with respect to methyl mercaptan: 91%.

By comparison, the following results were obtained utilizing the same total volume of catalyst present in a multi-tubular reactor consisting of 9 tubes of length 5 m and of diameter 50 mm and cooled by means of air and operated under the same conditions as in the system described above:

| | | |
|---|---|---|
| maximum T°C. | : | 510°C. |
| degree of conversion | : | 99% |
| selectivity | : | 80% |

It is, thus, apparent that in addition to the low selectivity obtained with the air cooled reaction system, the catalyst mixture was heated to a temperature of 510°C. at which the catalyst undergoes considerable deterioration.

EXAMPLE 2

In a system similar to that of Example 1, but consisting of 3 reactors each supplied with 47 moles/hour of methanol and operated under the following conditions:
$H_2S/CH_3OH$ molar ratio = 1.8,
T°C. at the inlet of the first reactor = 300°C., pressure = 8 bars,
the maximum temperature reached was 445°C., which is practically the maximum permissible temperature for the catalyst.

EXAMPLE 3

In an installation similar to that of Example 1 but wherein the 2 completion reactors were omitted and the reaction conditions were as follows:
$H_2S/CH_3OH$ molar ratio = 1.15,
T°C. at the inlet of the first reactor = 320°C.,
pressure = 8 bars,
the following results were obtained:
maximum temperature: 388°C.
degree of conversion of methanol: 82%
selectivity: 81%

EXAMPLE 4

In a system similar to that of Example 3 and under the following conditions:
$H_2S/CH_3OH$ molar ratio = 1.80,
T°C. at the inlet of the first reactor = 320°C.,
pressure = 2 bars,
the following results were obtained:
T°C. maximum: 375°C.,
conversion: 80.5%,
selectivity: 93.3%.

It is evident from the foregoing that by dividing the catalyst charge and by controlling the amount of reagents introduced into each catalyst bed, the maximum temperature in the system is maintained within the desired range without adversely affecting the conversion rate and the selectivity of the reaction.

Various embodiments and modifications of the invention have been described in the foregoing description and examples, and further modifications will be apparent to those skilled in the art. For instance, it is contemplated that various types of reactors can be employed which will permit the catalyst to be divided in accordance with the invention. Likewise, various catalysts and promoters may be substituted for those suggested herein. These and other analogous modifications, alterations and substitutions are included within the scope of the present invention as defined by the following claims.

What is claimed is:

1. In a catalytic process for the vapor phase synthesis of methyl mercaptan by the reaction of hydrogen sulfide and methanol, the improvement comprising dividing the catalyst charge into separate portions to establish at least three catalytic zones within the catalyst bed, introducing the total theoretical amount of hydrogen sulfide into the first of said catalytic zones, introducing preselected amounts of methanol reagent into said catalytic zones wherein the molar ratio of hydrogen sulfide to methanol is between about 1.10 to 2.5 whereby the temperature in each of said catalytic zones is maintained between about 280°C. and 450°C. and recovering the methyl mercaptan product exiting from said catalyst bed.

2. The process as defined by claim 1, wherein said process is continuous and is effectuated at elevated pressure and temperatures.

3. The process as defined by claim 2, wherein the pressure is between about 2.5 bars and 25 bars.

4. The process as defined by claim 2, wherein the temperature is between about 320°C. and 370°C. and the pressure is between about 7 bars and 12 bars.

5. The process as defined by claim 1, wherein said catalyst is an activated alumina catalyst having a specific surface area between about 100 and 350 m²/g.

6. The process as defined by claim 5, wherein said catalyst further includes in combination therewith a promoter.

7. The process as defined by claim 6, wherein said promoter is selected from the group consisting of metal sulfides, alkali metal salts and alkali metal oxides.

8. The process as defined by claim 7, wherein said promoter is selected from the group consisting of cadmium sulfide, potassium carbonate and potassium tungstate.

9. The process as defined by claim 1, wherein the number of catalytic zones ranges between about 3 and 15.

10. The process as defined by claim 1, wherein the methanol reagent introduced in said catalytic zones comprises a mixture of liquid and gaseous methanol.

11. The process as defined by claim 10, wherein the proportionate amounts of liquid and gaseous methanol reagent vary between about 60 and 40%, respectively, in at least some of said catalytic zones and between about 40 and 60%, respectively, in other of said catalytic zones.

12. The process as defined by claim 1, wherein equivalent amounts of methanol reagent are introduced into each of said catalytic zones.

13. The process as defined by claim 1, wherein different amounts of methanol reagent are introduced into each of said catalytic zones.

14. The process as defined by claim 1, wherein at least one of said catalytic zones is not charged with methanol reagent.

* * * * *